(12) United States Patent
Righi et al.

(10) Patent No.: US 6,712,788 B2
(45) Date of Patent: Mar. 30, 2004

(54) AUTOMATIC SAFETY SYRINGE

(76) Inventors: Nardino Righi, Via Cavour 7, 20047 Brugherio (Milan) (IT); Roberto Rossi, Via Delle Ande, 10, 20151 Milan (IT); Sergio Restelli, Via Quarto Peperino 333B, 00100 Rome (IT)

( * ) Notice: Subject to any disclaimer, the term of this patent is extended or adjusted under 35 U.S.C. 154(b) by 0 days.

(21) Appl. No.: 10/208,743

(22) Filed: Aug. 1, 2002

(65) Prior Publication Data

US 2003/0028151 A1 Feb. 6, 2003

(30) Foreign Application Priority Data

Aug. 3, 2001 (EP) ............................................. 01830525

(51) Int. Cl.[7] ................................................ A61M 5/32
(52) U.S. Cl. ..................................................... 604/110
(58) Field of Search .............................. 604/110, 162, 604/181, 187, 192, 195, 264, 272

(56) References Cited

U.S. PATENT DOCUMENTS

| 4,185,628 A | | 1/1980 | Kopfer | |
| 5,211,628 A | * | 5/1993 | Marshall | ..................... 604/110 |
| 5,273,541 A | | 12/1993 | Malenchek | |
| 5,328,484 A | | 7/1994 | Somers et al. | |
| 5,876,382 A | | 3/1999 | Erickson | |

FOREIGN PATENT DOCUMENTS

| EP | 0 911 046 A2 | 4/1999 |
| WO | 00/27450 | 5/2000 |

* cited by examiner

*Primary Examiner*—Brian L. Casler
*Assistant Examiner*—Kevin C. Sirmons
(74) *Attorney, Agent, or Firm*—Nixon & Vanderhye, P.C.; Frank P. Presta

(57) ABSTRACT

An automatic safety syringe comprising a syringe body, hollow on the side and open at the front and rear; and a plunger sliding inside the syringe body with an injection stroke extending from a retracted syringe-filling position to a forward syringe-emptying position, the plunger being provided at the rear with a shaft that can be operated manually and brought out of the syring body through the rear end thereof. An injection needle integral with a needle carrier is egageable with the fore end of the syringe body. A hooking device is connected to the shaft of the plunger, to hook the needle carrier when the shaft is at the end of the injection stroke. An automatic device causes automatic retraction of the shaft of the plunger when the injection has been completed. a locking device is operatively connected to the shaft to block forward movement thereof when it is in the retracted position after intervention of the automatic device.

10 Claims, 4 Drawing Sheets

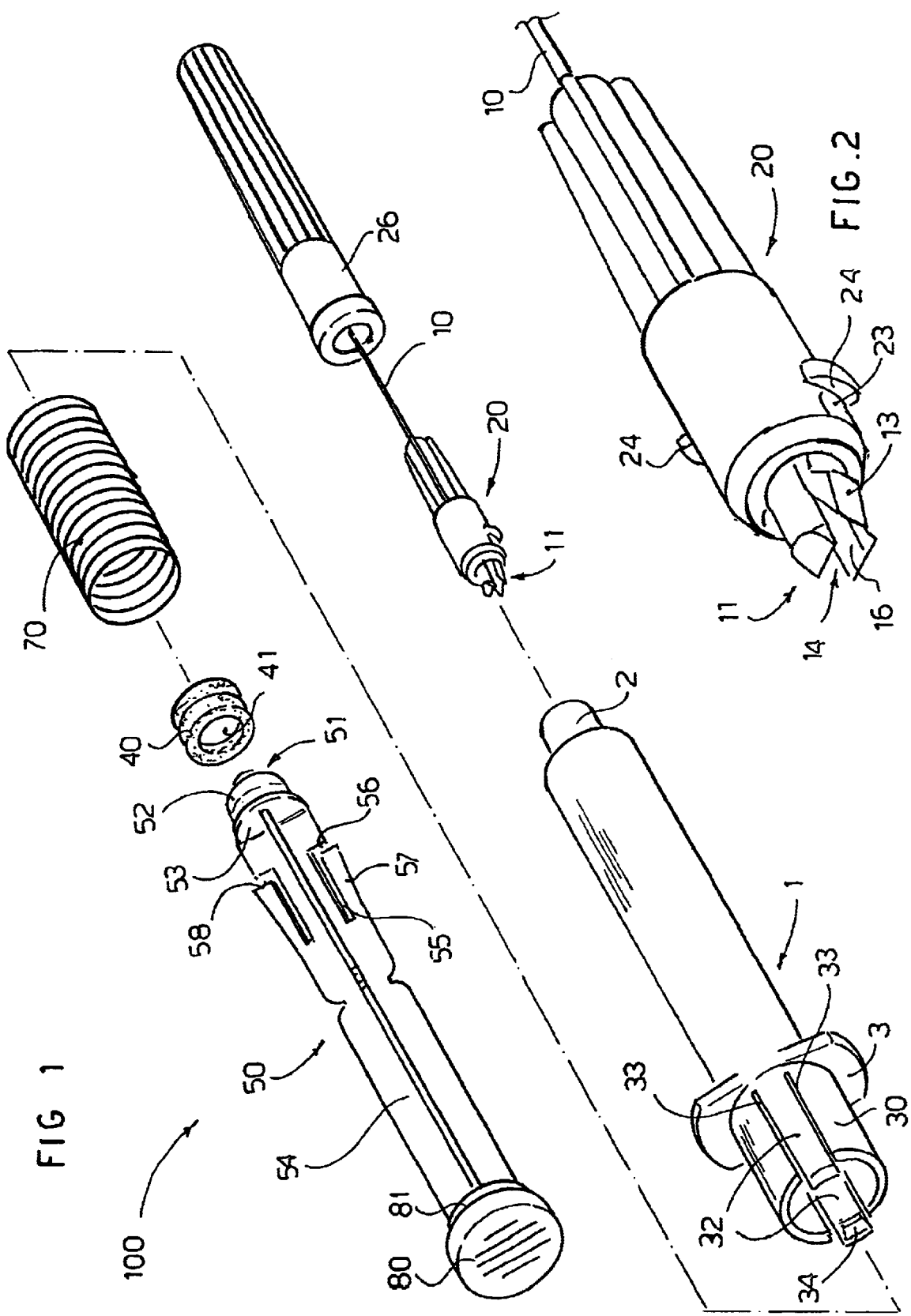

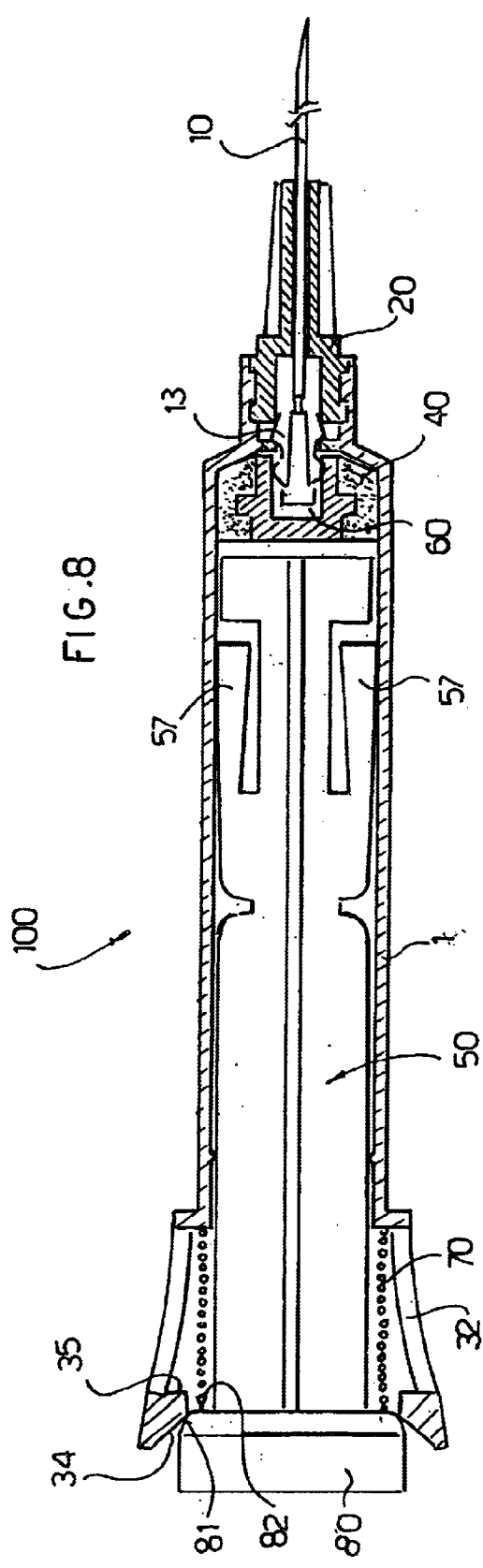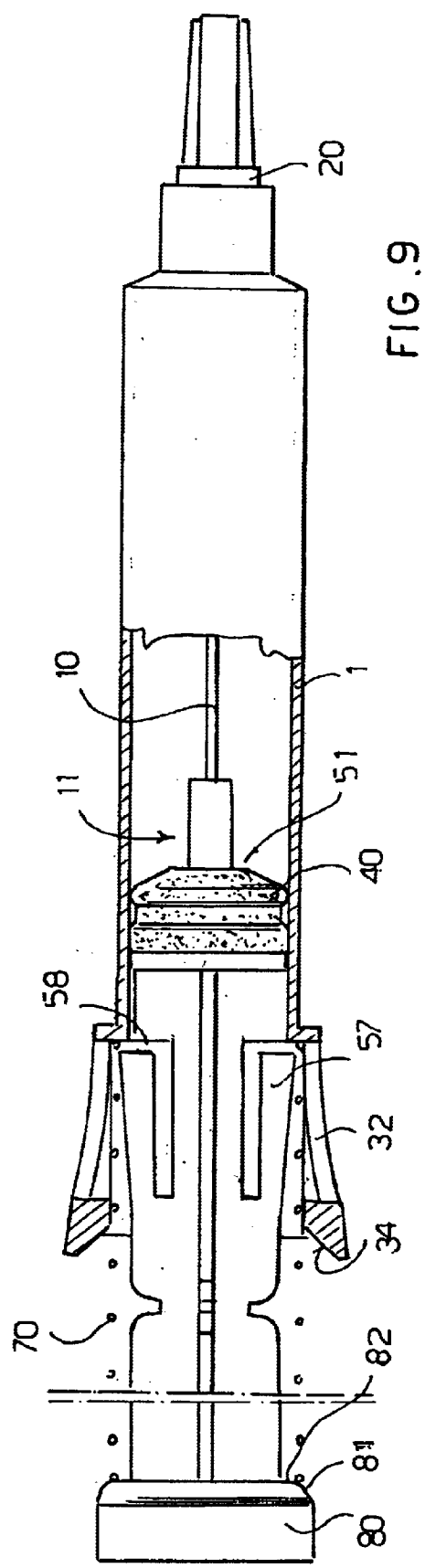

AUTOMATIC SAFETY SYRINGE

The present invention refers to an automatic safety syringe.

As is known, a syringe generally comprises a cylindrical body open at the rear to accommodate a plunger. A needle, hollow on the inside, is mounted a head end of the syringe body. By retracting the plunger the liquid contained in a vial is drawn into the syringe body through the needle. By pressing on the plunger the liquid contained inside the syringe body is injected, by means of the needle, into the patient's body.

To comply with safety regulations and to avoid the transmission of infectious diseases, syringes must generally be used just once and then discarded. For this reason there is growing demand on the market for disposable syringes able to prevent further use thereof.

Moreover, syringes generally present drawbacks from the point of view of safety. In fact, once the syringe has been used, the needle remains exposed at the head of the syringe body, with the risk of accidental injuries or needle sticks.

This drawback is overcome in part by European patent EP 0636381 which describes a protective device for syringe needles. In this case, when the plunger of the syringe reaches the end of its stroke, the fore end of the plunger shaft catches the needle. When the injection is completed the user must manually retract the shaft; in this manner the needle is pulled by the head of the shaft into a safety position inside the syringe body which avoids accidental needle sticks.

Said solution has problems during hooking of the needle carrier and has the drawback that the user, having completed the injection, can forget to carry out retraction of the shaft, leaving the needle exposed and thus rendering the protective device ineffective.

Patent application PCT WO 99/37345 describes a disposable safety syringe which provides a needle-covering sleeve axially mounted on the syringe body and sliding from a retracted position, in which it leaves the needle exposed to allow injection, to a forward position in which it completely covers the needle, preventing re-use of the syringe and acting as a protection against accidental needle sticks.

Once the injection has been completed, the sleeve is automatically carried in the safety forward position, by means of an automatic system and without any operating by the user. However, such a solution presents some problems for the provision and driving of an additional member, such as a needle-covering sleeve.

The object of the present invention is to eliminate the drawbacks of the prior art, providing a disposable safety syringe that is practical, versatile, cheap and simple to make.

Another object of the present invention is to provide such an automatic safety syringe that is able to prevent further attempts at use.

Yet another object of the present invention is to provide such an automatic syringe that is extremely safe and able to prevent accidental injuries or tampering after use thereof.

These objects are achieved in accordance with the invention with the characteristics listed in appended independent claim 1.

Advantageous embodiments of the invention are apparent from the dependent claims.

The disposable syringe according to the invention comprises a syringe body hollow on the inside and open at the front and rear, a plunger that can slide inside the syringe body so as to be movable from a retracted syringe-filling position to a forward syringe-emptying position, and an injection needle integral with a needle-carrier that can be engaged at the fore end of the syringe body. The plunger is provided at the rear with a shaft that can be operated manually and brought out of the syringe body through the rear end thereof. The syringe comprises an injection needle integral with a needle carrier that can be engaged directly or by means of a supporting body at the fore end of the syringe body.

A hooking device is provided such as to hook the needle carrier in order to pull it into the syringe body, when the plunger reaches the end of its stroke after the injection has been carried out.

Furthermore an automatic device is provided which allows the shaft of the piston to be retracted into a retracted position after the injection has been carried out and after the hooking device has hooked the needle.

The peculiarity of the invention lies in the fact that locking means operationally connected to the shaft of the plunger are provided to block forward movement of the shaft when it is in the retracted position, after the injection has been carried out and the automatic shaft retracting device has come into operation.

The advantages of the disposable syringe according to the invention are evident. In fact, once the injection has been completed, the hooking device intervenes to hook the needle carrier, the automatic device to cause retraction of the shaft which pulls the needle inside the syringe body and the locking device to block any attempt, voluntary or involuntary, to advance the plunger shaft, which would cause the needle to re-emerge from the head of the syringe body.

In this manner the needle always remains protected inside the syringe body, avoiding the risk of accidental needle sticks and the possibility of re-use of the syringe.

Further characteristics of the invention will be made clearer by the detailed description that follows, referring to a purely exemplary and therefore non-limiting embodiment thereof, illustrated in the appended drawings, in which:

FIG. 1 is an exploded axonometric view illustrating the automatic safety syringe according to the invention;

FIG. 2 is an enlarged, perspective view illustrating a needle carrier inserted in its supporting body;

FIG. 8 is a view like FIG. 7, in which the plunger is in a forward position near its forward end of stroke at the end of the injection;

FIG. 9 is a view like FIG. 7, in which the injection has been completed and automatic retraction of the plunger shaft has taken place.

Figure 3:
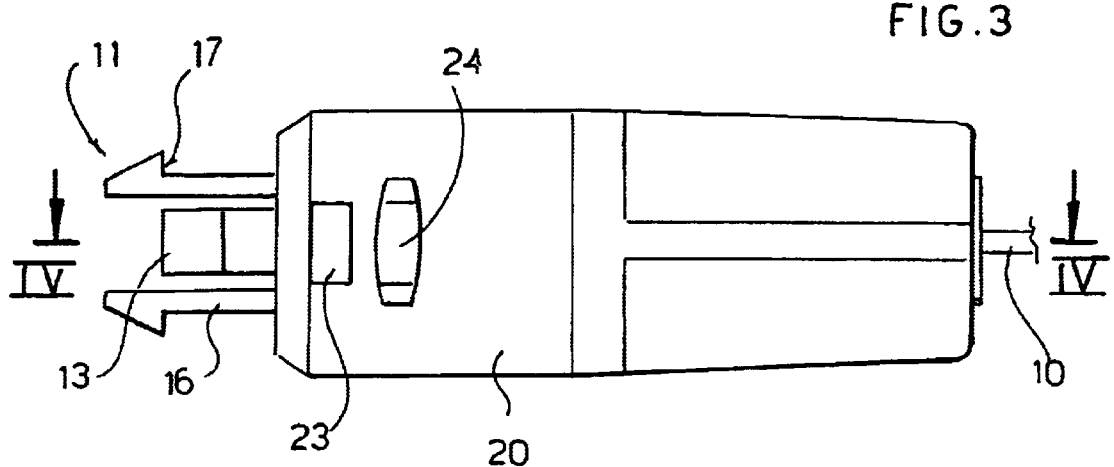
FIG. 3 is a side view of the needle carrier and supporting body assembly of FIG. 2.

The automatic safety syringe according to the invention, denoted as a whole with reference numeral 100, is described with the aid of the figures.

Figure 7:
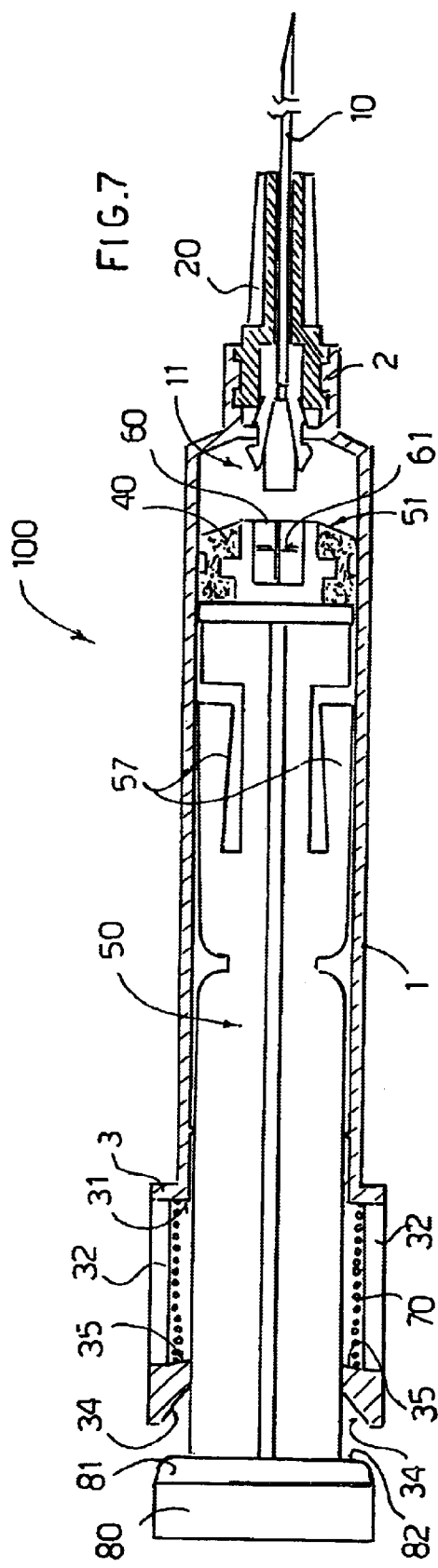
FIG. 7 is an axial sectional view illustrating the syringe of FIG. 1 assembled.

With reference for now to FIG. 1 in particular, the syringe 100 comprises a cylindrical body 1, hollow on the inside, defining a cylindrical chamber. The body 1 has a flange 3 which protrudes radially outward. A cylindrical rear part 30 of the body 1 axially open toward the outside is provided behind the flange 3. As shown in FIG. 7, the rear part 30 has an inside diameter slightly greater than the inside diameter of the body 1 of the syringe so as to define an annular abutment surface 31.

In the rear part 30 of the body two longitudinal tongues 32 disposed in diametrically opposite positions are provided. Each tongue 32 is obtained by means of two longitudinal incisions formed on the rear part 30 of the syringe body. The tongues 32 are flexible and can bend outward. Each tongue 32 has an inwardly tapered rear end 34 which defines an inwardly protruding part having an abutment surface 35 protruding radially inward from the inner surface of the tongue 32.

A spring 70 is retained inside the rear part 30 of the syringe body, compressed between the annular abutment surface 31 and the abutment surface 35 of the tongues 32.

Figure 6:
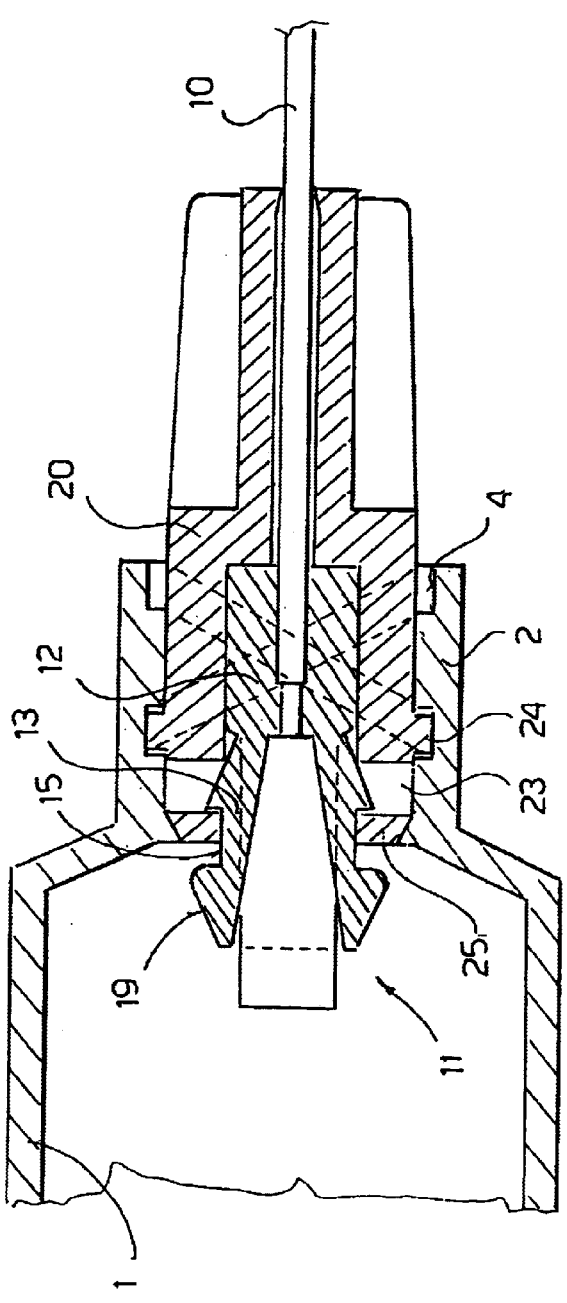
FIG. 6 is a view partially in axial section, broken off, showing the supporting body of the needle carrier mounted in the top of the syringe body.

The fore end of the body 1 is tapered and ends with an outwardly open head 2, in the form of a cylindrical tang, with a smaller diameter than the body 4. As shown better in FIG. 6, an inner thread 4 is formed in the inner surface of the head 2.

A needle 10 is supported by a needle carrier 11. As better shown in FIGS. 4 and 5, the needle carrier 11 comprises a cylindrical block 12 which has an axial hole to receive an end of the needle 10. The cylindrical block 12 has four flexible tongues comprising a first pair of opposed tongues 13, and a second pair of opposed tongues 16. The tongues 13 and 16 are disposed around an axial space 14 and are separated from one another by longitudinal slits of the space 14.

The two flexible tongues 13 of the first pair have a tapered outwardly protruding outer end surface 19 that defines an outwardly facing groove 15. The two flexible tongues 16 of the second pair have a tapered outwardly protruding end surface 18 which delimits an outwardly facing abutment surface 17. The tongues 13 of the first pair are slightly shorter than the tongues 16 of the second pair.

The needle carrier 11 is inserted in a supporting body 20. With reference to FIGS. 2 and 3, the supporting body 20 has a frustoconical shape, is hollow on the inside and has a cylindrical housing 21 axially able to accommodate the cylindrical block 12 of the needle carrier, said housing communicating with an axial channel 22 able to allow the passage of the needle 10 which emerges axially from the supporting body 20.

In the vicinity of the rear end of the supporting body 20 two radial slots 23 are disposed in diametrically opposite positions communicating with the housing 21 so as to delimit an edge part 25 at the rear end of the supporting body 20. In front of the radial slits 23 are two transverse tongues 24 which protrude radially outward from the outer side surface of the supporting body 20. The tongues 24 have such a thickness as to be able to engage inside the thread 4 provided inside the head 2 of the syringe body 1.

Figure 4:
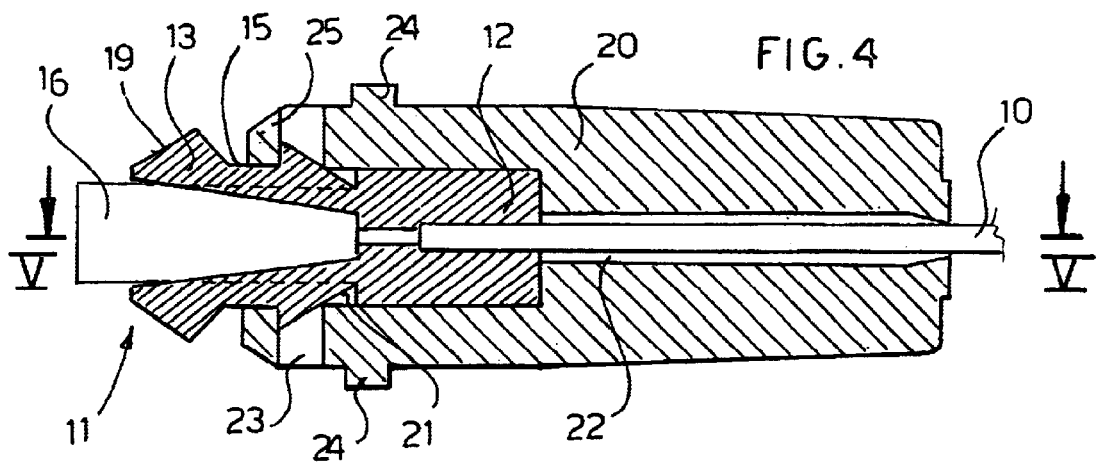
FIG. 4 is an axial sectional view along sectional plane IV—IV of FIG. 3.
Figure 5:
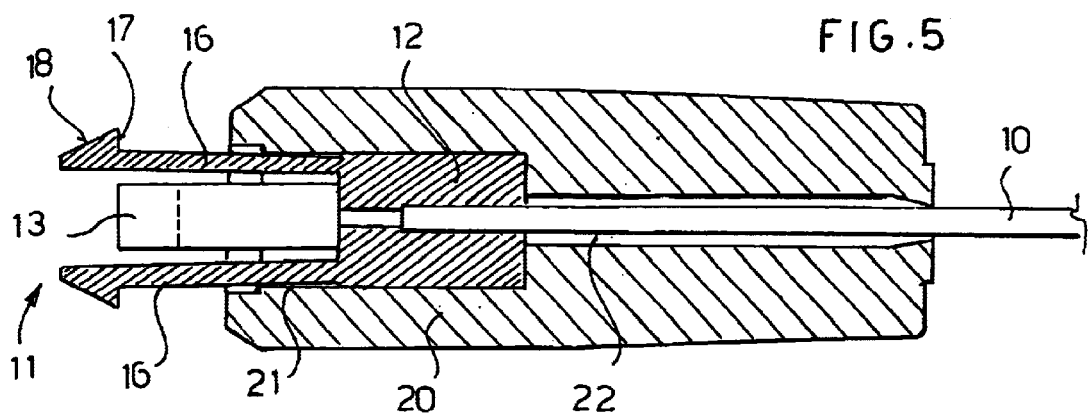
FIG. 5 is an axial sectional view along sectional plane V—V of FIG. 4.

As shown in particular in FIG. 4, the needle carrier 11 is inserted inside the supporting body 20 and in particular the protruding front part of each tongue 13 engages inside the respective radial slot 23 and the edge 25 of the supporting body 20 engages inside the two grooves 15 of the two tongues 13. In this manner the needle carrier 11 is firmly retained and held in an axial position inside the supporting body 20.

On compressing the tongues 13 inwardly the edge 25 of the supporting body 20 disengages from the grooves 15 of the tongues 13 and the needle carrier 11 can be extracted from the supporting body 20. In this manner the needle carrier 11 is of the interchangeable type and can be replaced according to the type of needle 10 to be used.

The needle carrier 11 and supporting body 20 assembly is mounted in the head 2 of the syringe body by screwing. To be precise, the radial tongues 24 of the supporting body are screwed into the inside thread 4 of the head 2 of the syringe body. The needle 10 is covered by means of a needle guard 26 (FIG. 1) which snap engages or screws into the cap 20.

A plunger 40 is made of plastic or rubber material and is of such a shape as to be able to slide tightly inside the chamber of the syringe body 1. The plunger 40 has an axial through cavity able to receive in engagement a head 51 of a plunger shaft 50.

The shaft 50 comprises an axial body part from which radially extend four longitudinal walls 54 at right angles to each other, so that the shaft 50 is substantially cross-shaped in section.

Two longitudinal tongues 57, disposed respectively on two diametrically opposed walls 54, are provided in the front part of the shaft 50. Each longitudinal tongue 57 is delimited by a longitudinal incision 55 and a transverse incision 56 on the respective wall 54. In normal conditions, the tongues 57 protrude slightly outward so that the end 58 of each tongue 57 defines an abutment surface outside the bulk of the side profile of the walls 54. The tongues 57 are flexible and can bend inward when the shaft is inside the chamber of the syringe body 1, and the tongues 57 are in contact with the inner wall of the syringe body.

The walls 54 are disposed between the head 51 and a rear flange 80. The rear flange 80 constitutes a resting surface for manual operation of the shaft of the syringe by the user. The flange 80 has in its front end an annular inwardly tapered surface 81 able to cooperate with the tapered surface 34 of the longitudinal tongues 32 of the rear part 30 of the syringe body. The tapered surface 81 of the rear flange 80 defines a radial abutment surface 82.

The head 51 has a first annular flange 52 which engages in an annular seat of the cavity 41 of the plunger and a second annular abutment flange 53 against which the base of the plunger 40 abuts.

As shown in FIG. 7, the head 51 of the shaft 50 has an outwardly open cylindrical seat 60. An annular ridge 61 protruding radially inward is provided inside the cylindrical seat 60. The annular ridge 61 is able to cooperate with the tapered surfaces 19 and 18 of the tongues 13 and 16, respectively, of the needle carrier 11.

Operation of the syringe 100 according to the invention will now be described.

In an initial situation the needle carrier 11 is mounted in the supporting body 20 with the edge 25 of the supporting body 20 engaged in the grooves 15 of the tongues 13 of the needle carrier 11. The supporting body 20 is mounted in the head 2 of the syringe body 1. The needle guard 26 is mounted on the supporting body 20 and keeps the needle 10 covered. The spring 70 is under compression inside the rear part 30 of the syringe body 1. The plunger 40 is mounted on the head of the shaft 50 and is inside the chamber of the syringe body 1. The longitudinal tongues 57 of the shaft 50, being in abutment with the inner surface of the chamber of the syringe body, are elastically bent inward.

Initially, the needle guard 26 is extracted, the needle 10 is positioned in the liquid to be aspirated, and the user retracts the shaft 50 by means of the operating flange 80 of the shaft 50. The consequent retraction of the plunger 40 causes a vacuum in the chamber of the syringe body 1, thus the liquid is drawn into the chamber of the syringe body 1 through the needle 10 and the syringe is substantially in the configuration shown in FIG. 7. Obviously the syringe could alternatively be pre-filled.

When the injection is performed, the user presses the rear part 80 of the shaft 50 causing a forward movement of the plunger 40 which pushes the liquid that is injected through the needle 10.

As shown in FIG. 8, when the plunger 40 arrives in the vicinity of the end of its stroke, the tapered end parts 19 and 18 of the tongues 13 and 16, respectively, of the needle carrier 11 enter the seat 60 of the head 51 of the shaft and come into contact with the annular ridge 61 provided inside the seat 60.

In particular, the outer tapered surface 18 of the tongues 16 and the outer tapered surface 19 of the tongues 13 slide on the annular ridge 61 and consequently the tongues 16 and the tongues 13 bend inward. When the plunger 40 reaches the end of its stroke, the annular ridge 61 passes the tapered outer surface 18 of the tongues 16. Consequently the tongues 16 snap outward and the abutment surface 17 of the tongues 16 engages with the annular ridge 61 of the head of the shaft. In this condition, the needle carrier 11 is hooked by the head of the shaft.

The tongues 13 also, sliding on the annular ridge 61, bend inward and, when the plunger has reached the end of its stroke, the grooves 15 of the tongues 13 disengage from the edge 25 of the supporting body 20. In this condition the needle carrier 11 is hooked to the head of the shaft and is no longer retained by the supporting body 20 which is integral with the head 2 of the syringe body.

When the plunger 40 is at the end of its stroke, the tapered surface 81 of the rear flange 80 of the shaft abuts against the tapered surface 34 of the end of the tongues 32 of the rear part 30 of the syringe body. Consequently the tongues 32 bend outward and one end of the spring 70 is no longer retained by the retaining surface 35. As a result the spring 70, which was compressed, is released and its free end abuts against the abutment surface 82 of the rear flange 80, causing automatic and involuntary retraction of the shaft 50.

Since the needle carrier 11 is constrained to the head 51 of the shaft 50, when the spring 70 causes retraction of the shaft 50, the needle 10 is pulled inside the chamber of the syringe body by the needle carrier, as shown in FIG. 9.

During automatic retraction of the shaft 50, when the free end 58 of the longitudinal tongues 57 of the shaft 50 goes beyond the abutment surface 31 inside the syringe body 1, substantially level with the flange 3 of the syringe body, the longitudinal tongues 57 bend outward, within the rear part 30 of the syringe body.

In this situation forward movement of the shaft 50 can no longer be caused, since the ends 58 of the tongues 57 would abut against the abutment surface 31 of the inner wall of the syringe body, preventing any attempt to push the shaft 50 forward. In this manner the needle 10 always remains protected inside the chamber of the syringe body and possible injury or attempts to re-use the syringe are avoided.

Numerous changes and modifications of detail within the reach of a person skilled in the art can be made to the present embodiment of the invention without departing from the scope of the invention, set forth in the appended claims.

What is claimed is:

1. A disposable syringe comprising:
   a syringe body having a hollow inside and having a front and rear that are open,
   a plunger sliding inside the syringe body and being movable from a retracted syringe-filling position to a forward syringe-emptying position, said plunger being provided at the rear with a shaft that can be operated manually and brought out of the syringe body through the rear end thereof,
   an injection needle integral with a needle carrier attachable, directly or by means of supporting body to the fore end of the syringe body,
   hooking means operatively connected to said shaft of the plunger, able to hook said needle carrier to pull it inside the syringe body,
   elastic means retained under compression within said syringe body,
   retaining means operatively connected to said syringe body to retain said elastic means under compression, and
   engagement means operatively connected to said shaft able to cooperate with said retaining means to free said elastic means when said plunger has reached the end of the injection stroke, so that said elastic means can act on said shaft to cause retraction thereof into the retracted position, and
   locking means operatively connected to said shaft to block forward movement of said shaft, when it is in the retracted position, after the injection has been performed, said locking means comprising flexible longitudinal tongues, and the inside of said syringe body having an abutment surface constructed to abut against the end of said tongues of the shaft, when said shaft is in the retracted position after the injection has been performed, to prevent a possible forward movement of said shaft.

2. A syringe according to claim 1, characterized in that said shaft comprises at least two longitudinal walls, disposed in diametrically opposite positions, and that said tongues are obtained by means of incisions on said at least two longitudinal walls.

3. A syringe according to claim 1, characterized in that said end of said tongue protrudes slightly outward with respect to the peripheral edge of said shaft and that said tongues are inwardly flexible, so as to bring the end of each tongue within the lateral bulk of the shaft, when the shaft is inside said chamber of the syringe body.

4. A syringe according to claim 1, characterized in that said abutment surface for said longitudinal flexible tongues of the shaft, is obtained by means of a rear part of the syringe body having an inside diameter slightly greater than the inner chamber of the syringe body.

5. A syringe according to claim 4, characterized in that said elastic means are disposed inside said rear part of the syringe body and said retaining means for the elastic means are elastic retaining tongues formed in said rear part of the syringe body.

6. A syringe according to claim 5, characterized in that each of said retaining tongues is obtained by means of two longitudinal incisions formed at the end of said rear part of the syringe body and said retaining tongues comprise an inwardly protruding part able to retain said elastic means under compression.

7. A syringe according to claim 6, characterized in that said engagement means are disposed at the rear end of said shaft and comprise a tapered annular surface able to cooperate with a tapered surface of said tongues causing outward bending of said retaining tongues so as to free an end of said elastic means retained by said protruding part of the retaining tongues.

8. A disposable syringe comprising:
   a syringe body having a hollow inside and having a front and rear that are open,
   a plunger sliding inside the syringe body and being movable from a retracted syringe-filling position to a forward syringe-emptying position, said plunger being provided at the rear with a shaft that can be operated manually and brought out of the syringe body through the rear end thereof, an injection needle integral with a needle carrier attachable, directly or by means of supporting body to the fore end of the syringe body, hooking means operatively connected to said shaft of the plunger, able to hook said needle carrier to pull it inside the syringe body, elastic means retained under compression within said syringe body, retaining means operatively connected to said syringe body to retain said elastic means under compression, engagement means operatively connected to said shaft able to cooperate with said retaining means to free said elastic means when said plunger has reached the end of the injection stroke, so that said elastic means can act on said shaft to cause retraction thereof into the retracted position, and locking means operatively connected to said shaft to block forward movement of said shaft, when it is in the retracted position, after the injection has been performed.

wherein said needle carrier comprises first engagement means able to engage directly with the fore end of the syringe body or with said supporting body able to be secured to the fore end of the syringe body and second engagement means able to engage with said hooking means.

9. A syringe according to claim 8, characterized in that said first engagement means of said needle carrier are a first pair of opposed tongues and said second engagement means of said needle carrier are a second pair of opposed tongues and said hooking means are an annular ridge protruding radially inward, disposed inside a seat formed at the fore end of said shaft and communicating with the outside.

10. A syringe according to claim 9, characterized in that said supporting body for the needle carrier comprises:

an inner housing able to accommodate a cylindrical block of said needle carrier, a rear edge able to be engaged by grooves formed in the outer surface of said first pair of tongues so as to retain the needle carrier, and transverse tongues protruding radially outward, so as to e able to be received in a thread formed in the inner surface of the syringe body to allow the supporting body to be screwed into the syringe body.

\* \* \* \* \*